United States Patent
Masotti et al.

(10) Patent No.: US 6,527,797 B1
(45) Date of Patent: Mar. 4, 2003

(54) LASER DEVICE FOR TREATMENT OF PAINFUL SYMPTOMATOLOGIES AND ASSOCIATED METHOD

(75) Inventors: Leonardo Masotti, Florence (IT); Francesco Muzzi, Florence (IT); Francesco Repice, Pistoia (IT); Cesare Paolini, Florence (IT)

(73) Assignee: El.En S.p.A. (IT)

( * ) Notice: Subject to any disclaimer, the term of this patent is extended or adjusted under 35 U.S.C. 154(b) by 0 days.

(21) Appl. No.: 09/325,165

(22) Filed: Jun. 3, 1999

Related U.S. Application Data

(63) Continuation-in-part of application No. 08/798,515, filed on Feb. 10, 1997.

(30) Foreign Application Priority Data

Feb. 13, 1996 (IT) .......................................... FI96A0026

(51) Int. Cl.⁷ .............................................. A61B 18/20
(52) U.S. Cl. .............................. 607/89; 607/88; 606/3; 606/10; 606/12; 606/17; 128/898
(58) Field of Search .................... 606/3–19; 607/88–96, 607/98–104; 128/907, 898

(56) References Cited

U.S. PATENT DOCUMENTS 4,930,504 A * 6/1990 Diamantopoulos et al. .... 606/3
4,931,053 A * 6/1990 L'Esperance ................... 606/2
5,755,752 A * 5/1998 Segal ........................... 607/89

FOREIGN PATENT DOCUMENTS

SU  1648471  * 5/1991  ................. 128/907

OTHER PUBLICATIONS

American Heritage Dictionary p. 375.*

* cited by examiner

Primary Examiner—David M. Shay
(74) Attorney, Agent, or Firm—McGlew and Tuttle, P.C.

(57) ABSTRACT

A device for laser treatment of painful symptomatologies with a first laser source 1, a conveying device for conveying the laser energy to a hand unit 5, and optical structure 11, 13 for defocusing the laser beam.

18 Claims, 1 Drawing Sheet

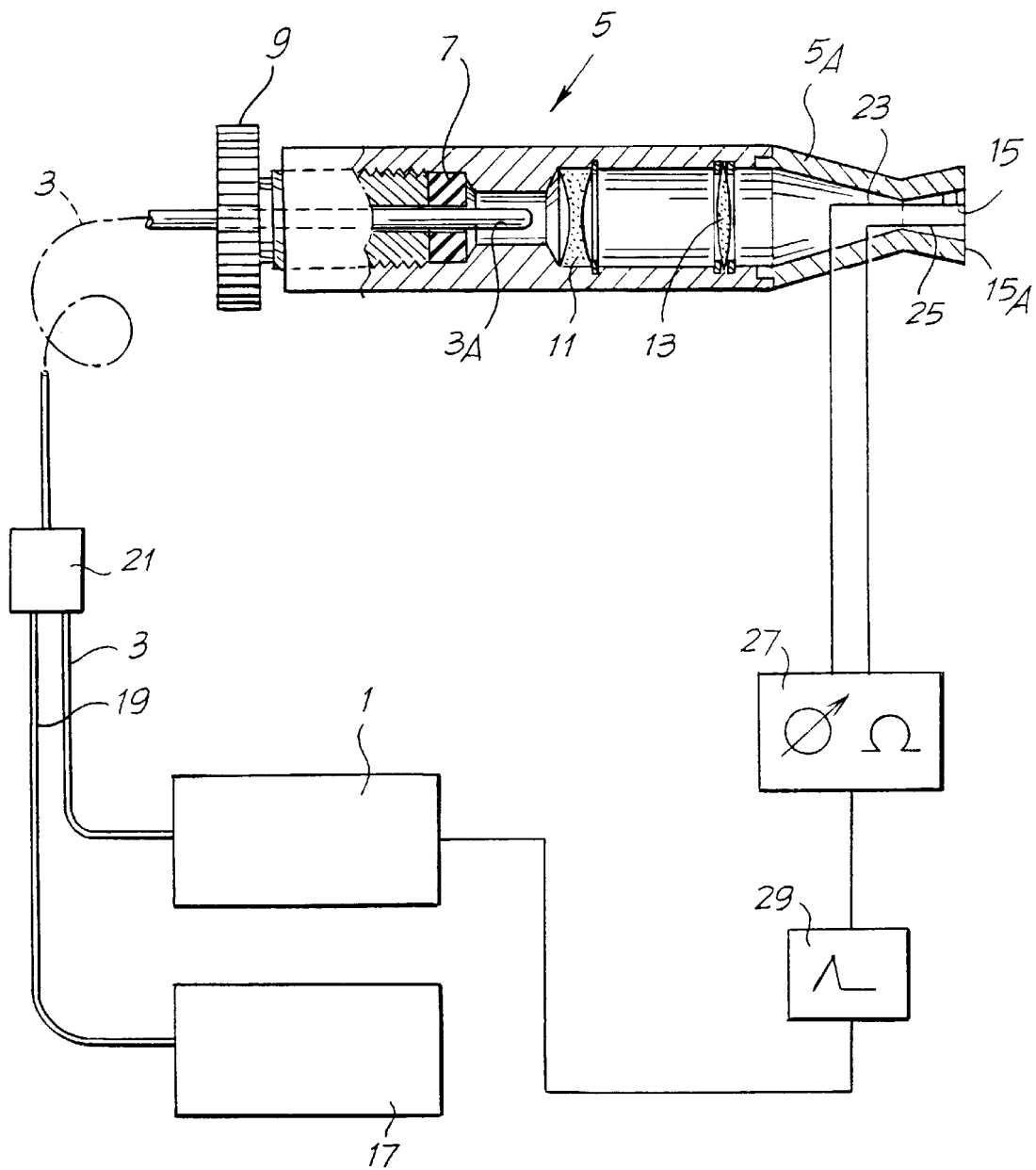

LASER DEVICE FOR TREATMENT OF PAINFUL SYMPTOMATOLOGIES AND ASSOCIATED METHOD

This is a continuation-in-part of application Ser. No. 08/798,515 filed Feb. 10, 1997, and the entire disclosure of this prior application is considered to be part of the disclosure of the accompanying application and is hereby incorporated by reference therein.

FIELD OF THE INVENTION

The present invention relates to a device for local treatment of symptomatologies by means of laser application, for example for use in physiotherapy.

BACKGROUND OF THE INVENTION

Use of lasers in medical and aesthetic applications is known.

In the more strictly therapeutic sector, the laser is used, for example, for conveying, through an endoscope and an optical fiber, a high-density beam of energy to the inside of an organ for the destruction of polyps by hyperthermia.

In the aesthetic field, the laser is used with low energy levels for anti-ageing treatment of the skin.

SUMMARY AND OBJECTS OF THE INVENTION

Essentially, the present invention is based on recognition of the fact that by applying an appropriately defocused laser beam within an appropriate range of wavelengths at given points of the epidermis of a patient afflicted by painful symptomatologies of various origins (deriving, for example, from past and recent traumas, arthrosis or rheumatism), the stimulation of the nerve ends by means of the incident energy causes a gradual reduction in, and in the end the disappearance, of the pain.

Therefore, the subject of the present invention is a device for laser treatment of painful symptomatologies, which comprises a first laser source, a first means of conveying the laser energy to a hand unit, and optical means of defocusing the laser beam which are positioned in the path of the laser beam.

Advantageously, the conveying means is constituted by an optical fiber, in front of the output end of which the optical means of defocusing are arranged.

It has been observed that particularly consistent effects and therefore rapid results in the reduction of painfll symptomatology are obtained by using a pulsed source which emits at a wavelength between 750 nanometers and 2.5 micrometers and preferably between 900 nanometers and 1.2 micrometers and with an energy level from 30 to 300 mjoules per pulse, and preferably between 100 and 200 mjoules per pulse. A particularly suitable laser source is the NDYAG laser with a wavelength of 1.06 micrometers. The frequency of the pulses as well as their duration are also parameters which have a considerable influence on the effectiveness of the treatment. It has been observed that the optimum frequency may optimally be selected between 10 and 40 Hz and preferably between 15 and 25 Hz for pulse durations which can vary between 100 and 200 microseconds. It is also preferable that only a single wavelength, for example 1.064 micrometers, be used to irradiate the body and treat the painful symptomatologies.

The hand unit can be held at the appropriate distance from the epidermis of the patient undergoing treatment by the operator. In order to make use safer and easier for the operator, however, the hand unit is in a preferred embodiment provided with a distance element to hold said optical means of defocusing at a predetermined distance from the body of a patient to whom the treatment is being applied, avoiding the necessity of determining and manually maintaining the optimum distance.

Again for the purpose of facilitating use of the device, it can be provided with a second laser source which emits at a wavelength in the visible range, and optical fiber or equivalent means for conveying the laser beam generated by said second source towards the hand unit.

The points where the application of the laser energy affords the major benefits, known as trigger points, are determined by the anatomical characteristics of the body. These are located, for example, in the region of the join between muscle and tendon. There is normally also a reduction in the thickness of the skin in this zone. Determination of the trigger point can be carried out on the basis of experience but this requires adequate knowledge of anatomy and can complicate the use of the device. Therefore, for the purpose of eliminating these disadvantages and of making the device easier to use, according to a particularly advantageous embodiment, a trigger point detector is provided, operating for example by measuring the resistance through the epidermis. In the region of the trigger points, in fact, resistance falls from normal values of around 200 kohms to values of a few kohms.

In one possible embodiment, the trigger point detector comprises a pair of electrodes associated with the hand unit, which during use are kept in contact with the body of the patient undergoing treatment and are connected to means for measuring the electric resistance between the electrodes. The measuring means bring about the generation of a control signal which orders the emission of a pulse or of a series of pulses from the laser source in the region of the detection of a trigger point.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The single FIGURE shows the hand unit of the device and, diagrammatically, the laser sources and the control systems.

DESCRIPTION OF THE PREFERRED EMBODIMENT

In the attached diagrammatic drawing, 1 indicates a laser source, for example, a NDYAG laser with emission at 1.06 micrometers, connected by means of an optical fiber 3 to a hand unit 5. Inside the hand unit, the output end 3A of the optical fiber 3 is fixed by means of an elastic sleeve 7 and a clamping nut 9. Arranged facing the end 3A of the optical fiber 3 is a defocusing optic 11, 13.

The hand unit 5 ends in a converging end 5A to which is fixed a distance piece 15 with a surface 15A which is brought into contact with the epidermis E of the patient to whom the treatment is being applied. In this way, the defocusing optic 11, 13 is always held at a predetermined distance from the epidermis. In this way, once fixed, the energy is determined only by the energy density.

A second laser source 17 which emits continuously at a wavelength in the visible range introduces a laser beam into the fiber 3 by means of an auxiliary optical fiber 19, a connector 21 and a mixer. As an alternative and equivalent, the second laser source can send the laser beam into a known device for coaxial mixing of the two laser beams. The two beams made coaxial are then sent to a known device for introduction into the fiber.

In this manner, the treatment zone is illuminated and can be seen by the operator in the presence of the distance piece 15 also if this is open or made of a transparent material.

Associated with the distance piece 15 are two electrodes 23, 25 connected to a resistance measuring device 27. This measures the resistance of the epidermis in the region of the zone of application of the hand unit 5 and, by means of a trigger signal generator 29, generates a control signal for the laser source 1 in such a manner that the latter emits pulses at the frequency and of the duration desired when the hand unit 5 is in the region of a trigger point, where the resistance measured by the measuring device 27 is lower.

It is intended that the drawing shows only an exemplary embodiment which is given only by way of practical demonstration of the invention, it being possible for the invention to vary in form and arrangement without moreover leaving the scope of the idea which forms the invention itself.

While specific embodiments of the invention have been shown and described in detail to illustrate the application of the principles of the invention, it will be understood that the invention may be embodied otherwise without departing from such principles.

What is claimed is:

1. A device for laser treatment of painful symptomatologies, the device comprising:
   a hand unit;
   a first pulsed laser source emitting a laser beam with laser energy at a wavelength between 0.9 and 2.5 micrometers, said first pulsed laser source having an energy level between 30 and 300 mJ (milli-joules) per pulse, said pulses having a duration between 100 and 200 microseconds, said pulses having a frequency between 10 and 40 Hz;
   an optical fiber connected to said hand unit and to said first pulsed laser source, said optical fiber conveying the laser energy of said first pulsed laser source to said hand unit, said optical fiber having an output end;
   an optical defocuser connected to said hand unit for defocusing the laser beam, said optical defocuser being positioned in the path of the laser beam of said first pulsed laser beam source in front of said output end of said optical fiber; and
   a distance element connected to said hand unit to hold said optical defocuser means at a predetermined distance from the body of the patient.

2. The device as claimed in claim 1, wherein;
   said distance element has one of an opening and a transparent portion for viewing portions of the body irradiated by said laser beam;
   said defocuser diverges the laser beam to a greater extent than the laser beam would diverge from said optical fiber.

3. The device as claimed in claim 1, wherein
   said wavelength of said laser source is between 1.6 micrometers and 2.5 micrometers.

4. The device as claimed in claim 1, further comprising a second laser source which emits at a wavelength in the visible range, and means for conveying the laser beam generated by said second source towards said hand unit, said means for conveying being connected to said second laser source and to said hand unit.

5. The device as claimed in claim 4, wherein said second laser source is connected with means for introducing the energy emitted by said second laser source into said optical fiber.

6. The device as claimed in claim 1, further comprising:
   a trigger point detector which emits a trigger point detection signal; and
   synchronization means for synchronization between said trigger point detection signal and the emission of a laser beam from said first laser source, said synchronization means being connected to one of said first laser source and said hand unit.

7. The device as claimed in claim 6, wherein said detector comprises:
   a pair of electrodes connected with said hand unit, said electrodes being maintained during use in contact with the body of a patient undergoing treatment; and
   measuring means connected to said electrodes for measuring the electric resistance between said electrodes, said measuring means bringing about the generation of a control signal which orders the emission of a pulse or a series of pulses from said first laser source.

8. A device for laser treatment of painful symptomatologies, the device comprising:
   a hand unit;
   a first pulsed Nd:YAG laser source emitting a laser beam with laser energy at a wavelength of 1.064 micrometers, said first pulsed laser source having an energy level between 30 and 300 mJ (milli-joules) per pulse, said pulses having a duration between 100 and 200 microseconds, said pulses having a frequency between 10 and 40 Hz;
   an optical fiber conveying the laser energy of said first pulsed laser source to said hand unit, said optical fiber having an output end;
   an optical defocuser for defocusing the laser beam, said optical defocuser being positioned in a path of the laser beam of said first pulsed laser beam source in front of said output end of said optical fiber; and
   a distance element to hold said optical defocuser means at a predetermined distance from the body of the patient.

9. The device as claimed in claim 8, further comprising a second laser source which emits at a wavelength in the visible range, and means for conveying the laser beam generated by said second source towards said hand unit.

10. The device as claimed in claim 9, wherein said second laser source is connected with means for introducing the energy emitted by said second laser source into said optical fiber.

11. The device as claimed in claim 8, further comprising:
    a trigger point detector which emits a trigger point detection signal; and
    synchronization means for synchronization between said trigger point detection signal and the emission of a laser beam from said first laser source.

12. The device as claimed in claim 11, wherein said detector comprises
    a pair of electrodes connected with said hand unit, said electrodes being maintained during use in contact with the body of a patient undergoing treatment;

measuring means for measuring the electric resistance between said electrodes, said measuring means bringing about the generation of a control signal which orders the emission of a pulse or a series of pulses from said first laser source.

13. A method for laser treatment of painful symptomatologies, the method comprising the steps of:

generating a laser beam with laser at a wavelength between 0.9 and 2.5 micrometers with an energy level between 30 and 300 mJ (milli-joules) per pulse, said pulses having a duration between 100 and 200 microseconds, said pulses having a frequency between 10 and 40 Hz;

conveying the laser energy to a handpiece;

defocusing the laser beam;

applying the defocused laser beam to a patient in need of said treatment in correspondence of a trigger point on the skin of said patient.

14. The method as claimed in claim 13, further comprising the step of:

locating said trigger point by means of measuring the resistivity on the epidermis using a measuring system with electrodes and wherein, when said measuring system locates a trigger point, it emits a signal to activate a laser source to emit one or more laser pulses in the region of said trigger point.

15. The method claimed in claim 13, wherein said wavelength of said laser source is between 1.6 micrometers and 2.5 micrometers.

16. A method for laser treatment of painful symptomatologies, the method comprising the steps of:

generating a laser beam with Nd:YAG laser source emitting a laser beam with laser energy at a wavelength of 1.064 micrometers with an energy level between 30 and 300 mJ (milli-joules) per pulse, said pulses having a duration between 100 and 200 microseconds, said pulses having a frequency between 10 and 40 Hz;

conveying the laser energy to a handpiece;

defocusing the laser beam;

applying the defocused laser beam to a patient in need of said treatment in correspondence of a trigger point on the skin of said patient.

17. The method as claimed in claim 16, further comprising the step of:

locating said trigger point by means of measuring the resistivity on the epidermis using a measuring system with electrodes and wherein, when said measuring system locates a trigger point, it emits a signal to activate a laser source to emit one or more laser pulses in the region of said trigger point.

18. A method for laser treatment of painful symptomatologies, the method comprising the steps of:

generating a laser beam with a Nd:YAG laser source emitting a laser beam with laser energy at a wavelength of 1.064 micrometers with an energy level between 30 and 300 mJ (milli-joules) per pulse, said pulses having a duration between 100 and 200 microseconds, said pulses having a frequency between 10 and 40 Hz;

conveying the laser energy to a handpiece;

defocusing the laser beam;

applying only the defocused laser beam to a patient in correspondence of a trigger point on the skin of said patient to treat the painful symptomatologies.

* * * * *